United States Patent
Walters et al.

(10) Patent No.: US 6,916,656 B2
(45) Date of Patent: Jul. 12, 2005

(54) NON-LINEAR AMPLITUDE DIELECTROPHORESIS WAVEFORM FOR CELL FUSION

(75) Inventors: Richard E. Walters, Columbia, MD (US); Derin C. Walters, Columbia, MD (US); Alan D. King, Highland, MD (US)

(73) Assignee: Cyto Pulse Sciences, Inc., Glen Burnie, MD (US)

( * ) Notice: Subject to any disclaimer, the term of this patent is extended or adjusted under 35 U.S.C. 154(b) by 0 days.

(21) Appl. No.: 10/487,235

(22) PCT Filed: Apr. 5, 2002

(86) PCT No.: PCT/US02/08239

§ 371 (c)(1),
(2), (4) Date: Oct. 25, 2004

(87) PCT Pub. No.: WO03/020915

PCT Pub. Date: Mar. 13, 2003

(65) Prior Publication Data

US 2005/0048653 A1 Mar. 3, 2005

Related U.S. Application Data

(60) Provisional application No. 60/315,936, filed on Aug. 31, 2001.

(51) Int. Cl.⁷ .......................... C12N 15/02; C12N 15/64

(52) U.S. Cl. ....................... 435/450; 435/461; 435/470; 435/471

(58) Field of Search ................................ 435/450, 461, 435/470, 471

(56) References Cited

U.S. PATENT DOCUMENTS 6,197,176 B1 * 3/2001 Pethig et al. ............... 204/643

* cited by examiner

*Primary Examiner*—James Ketter
(74) *Attorney, Agent, or Firm*—Marvin S. Townsend

(57) ABSTRACT

An object of the invention is to provide a method of treating biological cells prior to subjecting the biological cells to cell fusion pulses which includes the step of treating the biological cells with pre-fusion electric field waveforms which change amplitude in a non-linear way with respect to time, such that the biological cells are first aligned with a relatively low amplitude, long duration pre-fusion electric field waveform and then compressed with a relatively high amplitude, short duration pre-fusion electric field waveform resulting in increased cell membrane contact prior to being subjected to cell fusion. The non-linear pre-fusion electric field waveforms can change in a stepped way, in a continuous way, in a sigmoidal way, with step-wise increasing waveforms in adjacent steps, with step-wise increasing waveforms in non-adjacent steps, and in accordance with non-linear algorithms.

12 Claims, 6 Drawing Sheets

Non Uniform Field Movement

NON-LINEAR AMPLITUDE DIELECTROPHORESIS WAVEFORM FOR CELL FUSION

CROSS-REFERENCE TO RELATED APPLICATION

This application claims priority based upon copending U.S. Provisional Application Ser. No. 60/315,936, filed 31 Aug. 2001.

TECHNICAL FIELD

The present invention relates generally to methods and apparatus for fusing biological cells to one another. More specifically, the present invention provides methods and apparatus for treating biological cells with electrical fields, such that the biological cells are aligned and have increased cell membrane contact prior to being subjected to cell fusion.

BACKGROUND ART

If a neutrally charged biological cell is placed in a uniform electric field, such as provided by a pair of electrodes which are both planar, the biological cell does not move toward one electrode or another because the attractive forces from both electrodes are the same.

On the other hand, if a neutrally charged biological cell is placed in a non-uniform electric field, such as provided by two electrodes which are both not planar, as shown in PRIOR ART FIG. 1, the biological cell forms a dipole, is attracted to one electrode with greater attractive force than the other, and moves towards the electrode having the greater attractive force.

Such a use of a non-uniform electric field is used in dielectrophoresis, and the concept of using dielectrophoresis to align living cells, followed by a fusion/electroporation pulse, to fuse cells has been in the literature since early 1970's. This process is used to produce hybrids of two different cell types for therapeutic purposes, for hybridoma production for producing monoclonal antibodies, for nuclear fusion, and for producing other hybrid cells. Dielectrophoresis is the process of applying an electrical force on neutrally charged particles such as living cells. The force from dielectrophoresis results from applying a non-uniform electric field that separates charges inside the cells forming a dipole. After the dipole has been formed, the non-uniform electric field then moves the cells towards the highest or lowest electric field intensity. This movement is dependent on the relative conductivities and permittivities of the medium and the biological cells or particles. The dielectrophoretic force is a function of the electric field squared so electric field polarity is not important. The force is a function of the relative conductivities and permitivities of the medium and the particles or cells. The conductivities and permitivities are also a function of frequency of the applied electric field. Typically, an AC voltage wave, such as a sine wave, is applied across electrodes to produce this alternating electric field. The sine wave voltage, frequency, and duration are optimized for specific cell types. After the AC wave is applied to align the cells, one or more fusion/electroporation pulses are applied to form pathways in the cell membranes in which membranes from both cells commingle. These pathways permit the contents of the cells to mix forming a hybrid cell. Following the fusion pulses, another AC field can be applied to hold the cells together while the fused cells stabilize. In some cases, the AC voltage has been linearly increased or decreased to prevent damage to the cells due to a sudden application of a field.

Examples of cell fusion applications include hybridoma production and nuclear transfer. A recent application for electrofusion is to produce therapeutic hybrids for cancer immunotherapy. These hybrids are produced from cancer tumor cells and immune system dendritic cells in an ex vivo process. Each treatment requires a large number of viable hybrids, which results in a new requirement for high efficiency in the hybrid production process.

There are a number of techniques (electrical, mechanical, chemical) available to perform cell fusion. This invention relates to electrical means. The current electric art uses a voltage waveform generator connected to an electrode device. With respect to relevant known electrical, mechanical, and chemical techniques, the following U.S. Patents and published PCT application are of particular interest and are incorporated herein by reference:

| | | |
|---|---|---|
| 4,326,934 | Apr. 27, 1982 | Pohl |
| 4,441,972 | Apr. 10, 1982 | Pohl |
| 4,764,473 | Aug. 16, 1988 | Matschke et al |
| 4,784,954 | Nov. 15, 1988 | Zimmermann |
| 5,304,486 | Apr. 19, 1994 | Chang |
| 6,010,613 | Jan. 4, 2000 | Walters et al |
| WO 00/60065 | Oct. 12, 2000 | Walters et al |

From the above, it is known to use pre-fusion electric field waveforms that have either a constant amplitude, see PRIOR ART FIG. 3, or a linearly increasing amplitude, see PRIOR ART FIG. 4. FIG. 5 illustrates an overall general PRIOR ART protocol for carrying out cell fusion using electric field waveforms, wherein a pre-fusion electric field waveform is followed by a fusion/electroporation pulse, which is followed by a post-fusion electric field waveform.

Nevertheless, efficiency of cell fusion following a constant amplitude or a linearly increasing amplitude of pre-fusion electric field waveforms cannot deliver the higher efficiencies required in such applications as therapeutic hybrid production for cancer immunotherapy. In this respect, it would be desirable if pre-fusion electric field waveforms were provided for biological cells which increases cell fusion efficiency over biological cells treated with a constant amplitude or a linearly increasing amplitude pre-fusion electric field waveform.

More specifically with respect to U.S. Pat. No. 5,304,486 of Chang, it is noted that FIG. 2E of Chang discloses a linear low voltage presine AC waveform, a high voltage linear electroporating AC waveform, and a low voltage linear post-poration AC waveform. The invention of Chang is confined solely to the fusion/electroporation pulses. Chang discloses only a linear, low voltage presine AC waveform. Chang does not disclose a non-linear low voltage presine AC waveform. Chang does not focus attention on the presine AC waveform, other than a nominal statement thereof.

The first process in any cell fusion system is to bring the cells into contact. In any case, sufficient force must be applied to each cell to overcome the negative surface charge. Merely applying a uniform electric field will not move a cell because the net charge of the cell is zero. Thus from the definition of electric field, there is no force applied:

Force=(Electric Field)*(Charge)

However, a non-uniform field moves the positive ions inside each cell to one side and the negative ions to the opposite side producing a dipole, as shown in PRIOR ART FIG. 1. Once the dipole is induced, a net force is exerted, on the cell because the intensity of the field is greater on one side than the other. The movement of cells in one direction causes the cells to concentrate in an area. Since the cells are now dipoles, the negative side of one cell will attract the positive side of another cell overcoming the negative surface charge, as shown in PRIOR ART FIG. 2. The non-uniform electric field is produced by the electrode device. The non-uniformity is a function of the electrode configuration, as shown in PRIOR ART FIGS. 1 and 2.

Generally, the cell types to be fused are placed in a low conductive medium (less than 0.01 S/m) to minimize ohmic heating that may harm the cells and that causes turbulence thus reducing the number of fused hybrids. In this respect, it would be desirable for biological cells being subjected cell fusion to be treated so as to reduce heating during cell alignment and cell membrane contact.

The waveform generator has two functions. The first is to produce the AC voltage waveform that is converted into an AC field by the electrode device. This AC field then brings the cells into alignment/contact. The second function is to produce a pulse voltage that electroporates the cell membrane, fusing the cells. In some cases another AC voltage is produced after the fusing pulse to hold the cells in alignment until the fusion products become viable or stable.

One of the factors for successful fusion is the membrane contact between the adjacent cells. The closer this contact before the fusion pulse is applied, the higher the efficiency of fusion. In U. Zimmermann, et al., "Electric Field Induced Cell to Cell Fusion", J. Membrane Biol. 67, 165–182 (1982), Zimmermann points out that increasing the AC wave electric field strength just before the fusion pulse may be the optimum approach. Clearly, it would be desirable for biological cells that are to undergo cell fusion to be pretreated with pre-fusion electric field waveforms which bring abort increased cell membrane contact without turbulence or heating.

In addition, there are a number of reasons why it is not desirable to immediately provide a high amplitude alignment waveform to cells that are to undergo cell fusion. A first reason is a mechanical reason. That is, immediate application of a high amplitude alignment waveform causes extreme force to be exerted on the cells, causing the cells to move rapidly towards an electrode. This rapid cell movement causes turbulence forces in the medium surrounding the cells. The turbulence forces do not allow complete pearl chains of cells to form, and the turbulence forces cause already formed pearl chains of cells to break up.

A second reason why it is not desirable to immediately provide a high amplitude alignment waveform to cells that are to undergo cell fusion is that such a high amplitude alignment waveform causes heating to occur in the media in which the biological cells are suspended. Heating also causes turbulence which does not permit complete pearl chains of aligned cells to form and causes already formed pearl chains to break up. The heat in the heated up media also reduces cell viability.

In view of the above, it would be desirable to avoid the mechanical forces, turbulence, and heating which result from immediately applying a high amplitude alignment waveform to biological cells that are to undergo cell fusion.

Thus, while the foregoing body of prior art indicates it to be well known to use pre-fusion electric field waveforms prior to carrying out cell fusion with en electroporation pulse, the prior art described above does not teach or suggest a dielectrophoresis waveform for cell fusion which has the following combination of desirable features: (1) provides pre-fusion electric field waveforms for biological cells which increase cell fusion efficiency over biological cells treated with a constant amplitude or a linearly increasing amplitude pre-fusion electric field waveforms; (2) avoids the mechanical forces, turbulence, and heating which result from immediately applying a high amplitude alignment waveform to biological cells that are to undergo cell fusion; (3) reduces heating of biological cells being treated with pre-fusion electric field waveforms for increasing cell alignment and cell membrane contact prior to being subjected to cell fusion; and (4) increase cell membrane contact between biological cells treated with pre-fusion electric field waveforms prior to undergoing cell fusion. The foregoing desired characteristics are provided by the unique non-linear dielectrophoresis waveform for cell fusion of the present invention as will be made apparent from the following description thereof. Other advantages of the present invention over the prior art also will be rendered evident.

Additional U.S. patents that are of interest include:

| 4,561,961 | Dec. 31, 1985 | Hofmann |
| 5,001,056 | Mar. 19, 1991 | Snyder et al |
| 5,589,047 | Dec. 31, 1996 | Coster et al |
| 5,650,305 | Jul. 22, 1997 | Hui et al |

Additional literature references include:
1. R. Bischoff, et al., "Human Hybridoma Cells Produced by Electro-Fusion", Fed. Eur. Biochem. Soc. Lett. 147, 64–68 (1982).
2. L. Changben, et al., "Use of Human Erythrocyte Ghosts for Transfer of 125.sub.I-BSA and 125.sub.I-DNA into Animal Cells from Cell Fusion", Scientia Sinica (Series B) 25, 680–865 (1982).
3. C. S. Chen, et al., "Biological Dielectrophoresis: The Behavior of Lone Cells in a Non-uniform Electric Field", Ann. N.Y. Acad. Sci. 238, 176–185 (1974).
4. Coster, H. G. L. and Zimmermann, U. "Direct Demonstration of Dielectric Breakdown in the Membranes of Valonia utricularis. " Zeitschrift fur Naturforschung. 30 c, 77–79.1975.
5. Coster, H. G. L. and Zimmermann, U. "Dielectric Breakdown in the Membranes of Valonia utricularis: the role of energy dissipation". Biochimica et Biophysica Acta. 382, 410–418, 1975.
6. Coster, H. G. L. and Zimmermann, U. "The mechanisms of Electrical Breakdown in the Membranes of Valonia utricularis." Journal of Membrane Biology. 22, 73–90, 1975.
7. K. Kaler, et al., "Dynamic Dielectrophoretic Levitation of Living Individual Cells", J. Biol. Phys. 8, 18–31 (1980).
8. A. R. Murch; et al., "Direct Evidence that Inflammatory Multi-Nucleate Giant Cells Form by Fusion", Pathol. Soc. Gr. Brit. Ire. 137, 177–180 (1982).
9. Neumann, B et al. "Cell Fusion Induced by High Electrical Impulses Applied to Dictyostelium", Naturwissenschaften 67, 414, 1980
10. Petrucci, General Chemistry: Principles and Modern Applications, 4th ed., p. 621, 1985 (no month).
11. Zimmermann et al., Electric Field-Induced Cell-to-Cell Fusion, The Journal of Membrane Biology, vol. 67, pp. 165–182 (1982) [no month].
12. Pohl, H. "Dielectrophoresis", Cambridge University Press, 1978.
13. H. A. Pohl, "Biophysical Aspects of Dielectrophoresis", J. Biol. Phys. 1, 1–16 (1973).

14. H. A. Pohl, et al., "Continuous Dielectrophoretic Separation of Cell Mixtures", Cell Biophys. 1, 15–28 (1979).
15. H. A. Pohl, et al., "Dielectrophoretic Force", J. Biol. Phys. 6, 133 (1978).
16. H. A. Pohl, et al., "The Continuous Positive and Negative Dielectrophoresis of Microorganisms", J. Bio. Phys. 9, 67–86 (1981).
17. Sale, J. H. and Hamilton, W. A. "Effects of High Electric Fields on Micro-Organisms", Biochimica et Biophysica Acta. 163, 37–43, 1968.
18. Sepersu, E. H., Kinosita, K. and Tsong, T. Y. "Reversible and Irreversible Modification of Erythrocyte Membrane Permeability by Electric Fields" Biochimica et Biophysica Acta. 812, 779–785, 1985.
19. J. Vienken, et al., "Electric Field-Induced Fusion: Electro-Hydraulic Procedure for Production of Heterokaryon Cells in High Yield", Fed. Eur. Biomed. Soc. Lett. 137, 11–13 (1982).
20. H. Weber, et al., "Enhancement of Yeast Protoplast Fusion by Electric Field Effects", A Preprint for Proceedings of the Fifth International Symposium on Yeasts, London, Ontario, Canada, Jul. 80.
21. Zimmermann, U. "Electrical Field Mediated Fusion and Related Electrical Phenomena", Biochimica et Biophysica Acta. 694, 227–277. 1982.
22. Zimmermann, U. et al "Fusion of Avena Sativa Mesophyll Proptoplasts by Electrical Breakdown", Biochimica et Biophysica Acta. 641, 160–165, 1981, 1982.
23. U. Zimmermann, et al., "Electric Field-Induced Release of Chloroplasts from Plant Protoplasts", Naturwissen 69, 451 (1982).
24. U. Zimmermann, et al., "Electric Field-Mediated Cell Fusion", J. Biol. Phys. 10, 43–50 (1982).
25. U. Zimmermann, "Cells with Manipulated Functions: New Perspectives for Cell Biology, Medicine, and Technology", Angew. Chem. Int. Ed. Engl. 20, 325–344 (1981).

DISCLOSURE OF INVENTION

The present invention is an improvement over the current art. With the present invention, a non-linear voltage waveform having a non-linear change in amplitude is applied to biological cells before application of one or more cell fusion/electroporation pulses. The present invention first brings about or forces tangential membrane contact and alignment between adjacent cells as a result of applying the non-linear voltage waveform. Then, the present invention brings about or forces close membrane contact between adjacent cells as a result of further application of the non-linear voltage waveform. In this respect, the biological cells 10 are compressed against each other under the influence of the waveform with a non-linear change in amplitude. The biological cells can be similar Eukaryotic cells, or they can be dissimilar Eukaryotic cells.

The pre-fusion non-linear voltage waveform, which changes in amplitude in a non-linear way, can be a non-linear AC voltage waveform. The AC electric field waveforms can include sine waves. A parameter of the non-linearity of the change in amplitude of the waveform can be set so that the fusion process can be optimized by cell type. With the amplitude of the AC waveform varying non-linearly in amplitude over time, the biological cells align and fuse with lower energy (less heating) and with higher fusion efficiency.

Preferably, the pre-fusion electric field waveform includes a relatively low amplitude, long duration electric field waveform followed by a relatively short duration, high amplitude electric field waveform. More specifically, the relatively low amplitude, long duration electric field waveform slowly facilitates pearl chain formation and alignment of biological cells without causing turbulence or cell death. Once the cells are aligned and in pearl chains, a relatively high amplitude, short duration pre-fusion electric field waveform is applied to the biological cells. The cells are already in alignment, and for a short period of time, before heating occurs, cell compression takes place without turbulence.

The pre-fusion electric field waveform amplitude can change in a stepped non-linear way with respect to time. The pre-fusion electric field waveform can change in amplitude in a continuous non-linear way with respect to time.

The pre-fusion electric field waveform includes an AC electric field waveform which changes in amplitude in a non-linear way with respect to time. The amplitude of the AC electric field waveform can change in a non-linear way with respect to time in accordance with a non-linear algorithm.

Preferably, the AC electric field waveforms have an AC waveform electric field intensity between 10 volts/cm and 1,000 volts/cm.

The non-linear step-wise amplitude increasing waveforms can be applied as pre-fusion electric field waveforms in either adjacent steps or non-adjacent steps.

Subsequent to applying the pre-fusion electric field waveform which changes in amplitude in a non-linear way, the biological cells are subjected to a cell fusion pulse. In addition, the biological cells can be treated with a non-linear AC electric field waveform following the cell fusion pulse.

There are a number of embodiments of a non-linear waveform whose amplitude changes in a non-linear way with respect to time such as wherein a pre-fusion type of AC amplitude changes with time. Examples of algorithms that can be used for the non-linear change in amplitude over time include exponential, logarithmic, polynomial, power function, step function, sigmoid function, and non-linear algorithms generally, etc.

In view of the above, an object of the present invention is to provide a new and improved non-linear pre-fusion electric field waveform whose amplitude changes in a non-linear way with respect to time as a dielectrophoresis waveform prior to cell fusion.

Another object of the invention is to provide a non-linear dielectrophoresis waveform for cell fusion in which AC electric field waveforms applied to the biological cells increase cell fusion efficiency over biological cells treated with a constant amplitude or a linearly increasing amplitude pre-fusion electric field waveform.

Yet another object of the present invention is to provide a new and improved non-linear dielectrophoresis waveform for cell fusion which reduces heating of biological cells being treated with pre-fusion electric field waveforms, for increasing cell alignment and cell membrane contact prior to being subjected to cell fusion.

Still another object of the present invention is to provide a new and improved non-linear dielectrophoresis waveform for cell fusion that avoids the mechanical forces, turbulence, and heating which result when the biological cells are subjected to a cell fusion from immediately applying a high amplitude alignment waveform to biological cells that are to undergo cell fusion.

Even another object of the present invention is to provide a new and improved non-linear dielectrophoresis waveform for cell fusion that increases cell membrane contact between biological cells treated with pre-fusion electric field waveforms prior to undergoing cell fusion.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein.

MODES FOR CARRYING OUT THE INVENTION

A method and apparatus are provided for non-linear dielectrophoresis waveform for cell fusion, and with reference to the drawings, said method and apparatus are described below.

Figure 1:
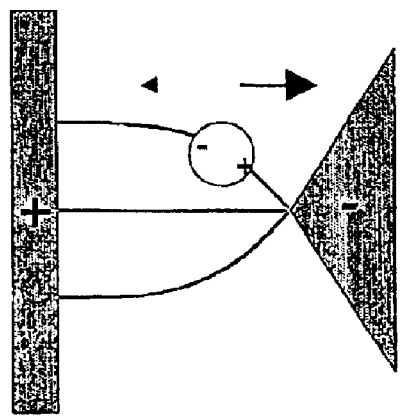
FIG. 1 illustrates PRIOR ART dipole formation in biological cells under the influence of a non-uniform electric field created by non-symmetrical electrodes.
Figure 2:
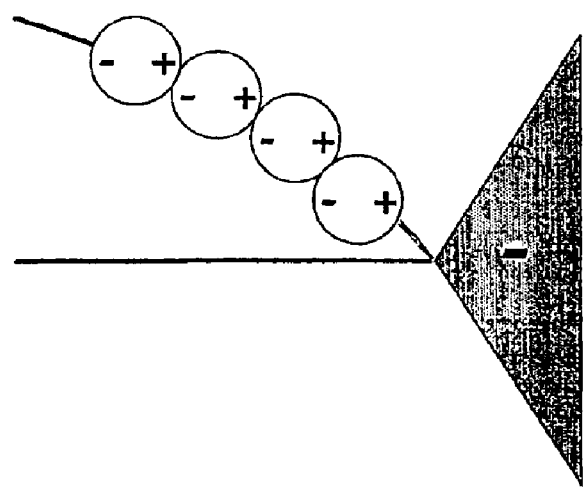
FIG. 2 illustrates a PRIOR ART path of movement of a biological cell in a non-uniform electric field created by non-symmetrical electrodes and also illustrates pearl chain alignment and formation of biological cells.
Figure 3:
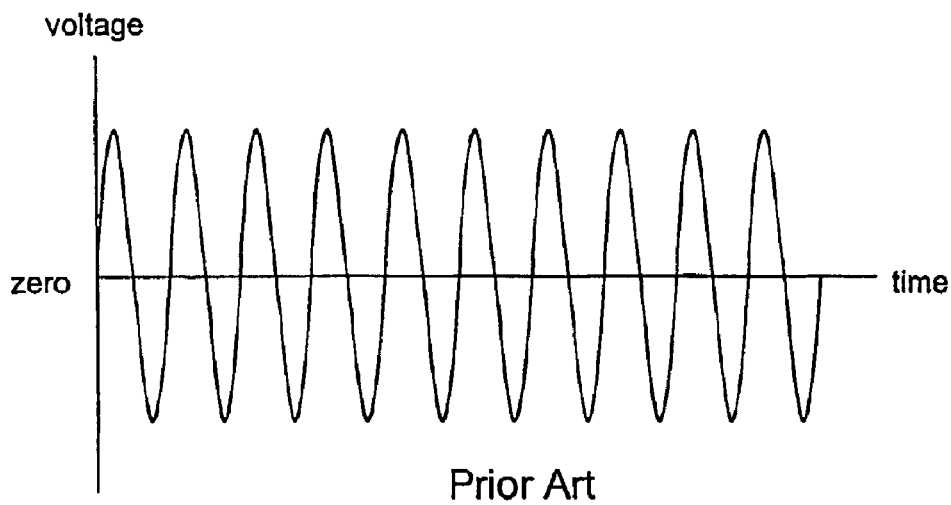
FIG. 3 illustrates PRIOR ART a constant amplitude pre-fusion electric field waveform.
Figure 4:
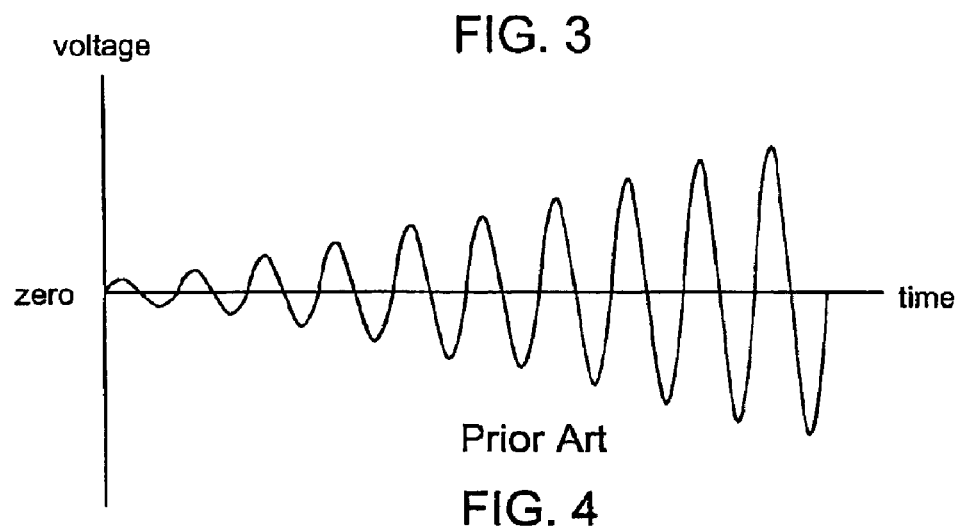
FIG. 4 illustrates PRIOR ART a linearly increasing amplitude pre-fusion electric field waveform.
Figure 5:
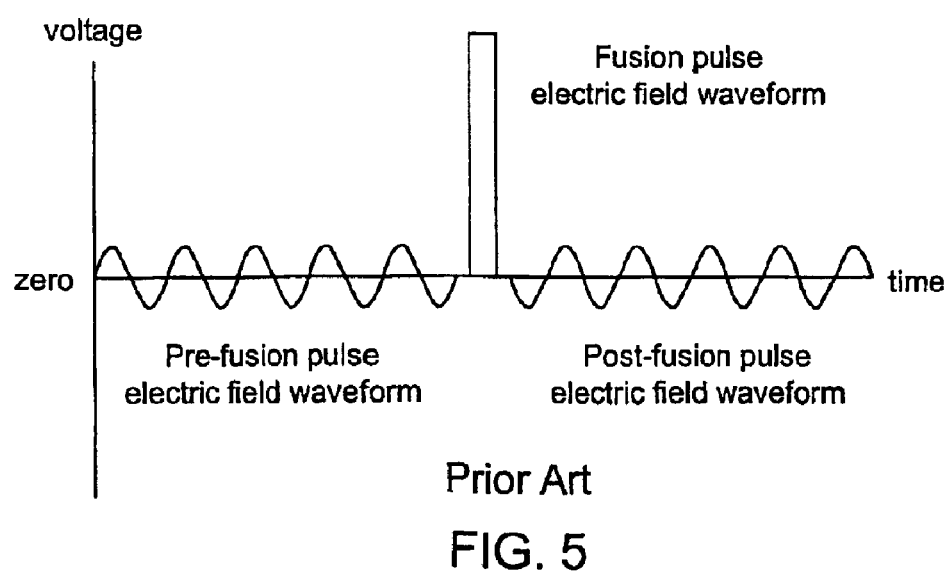
FIG. 5 illustrates an overall general PRIOR ART protocol for carrying cut cell fusion using electric field waveforms, wherein a pre-fusion electric field waveform is followed by a fusion/electroporation pulse, which is followed by a post-fusion electric field waveform.
Figure 6:
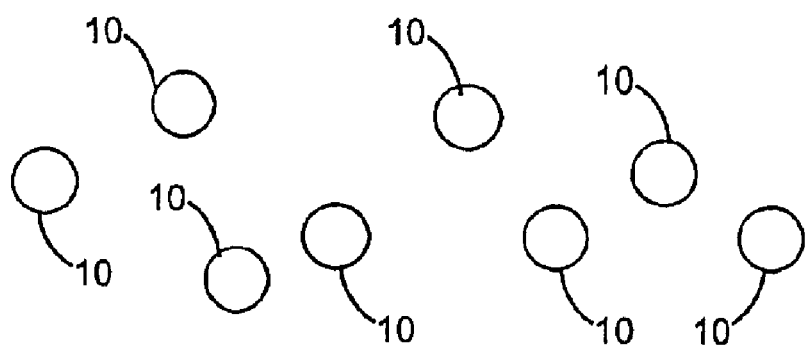
FIG. 6 shows independent biological cells prior to applying non-linear dielectrophoresis waveforms of the invention.
Figure 7:
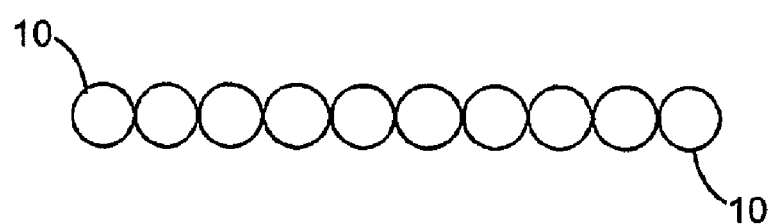
FIG. 7 shows tangentially contacting biological cells in pearl chain alignment during application of a relatively low amplitude, long duration pre-fusion electric field waveform of the invention.
Figure 8:
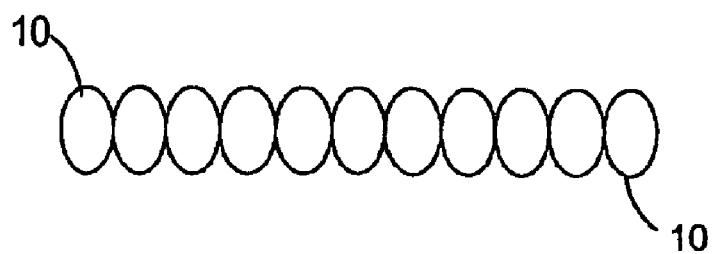
FIG. 8 shows closely contacting and compressed biological cells during application of a relatively high amplitude, short duration pre-fusion electric field waveform of the invention, following the application of the relatively low amplitude, long duration pre-fusion electric field waveform that was applied in FIG. 7.

The present invention is an improvement over the current art. With the present invention, a non-linear voltage waveform, whose amplitude changes in a non-linear way, is applied to biological cells before application of one or more cell fusion pulses. Separated biological cells 10 are shown in FIG. 6. The present invention first brings about or forces tangential membrane contact between adjacent cells as a result of applying the non-linear voltage waveform, as shown in FIG. 7. Then, the present invention brings about or forces close membrane contact between adjacent cells as a result of applying the non-linear voltage waveform, as shown in FIG. 8. As shown in FIG. 8, the biological cells 10 are compressed against each other under the influence of the non-linear voltage waveform.

The non-linear voltage waveform, whose amplitude changes in a non-linear way, can be a non-linear AC voltage waveform. A parameter of the non-linearity of the waveform can be set so that the fusion process can be optimized by cell type. With the amplitude of the AC waveform varying non-linearly over time, the biological cells align and fuse with lower energy (less heating) and with higher fusion efficiency.

Figure 10:
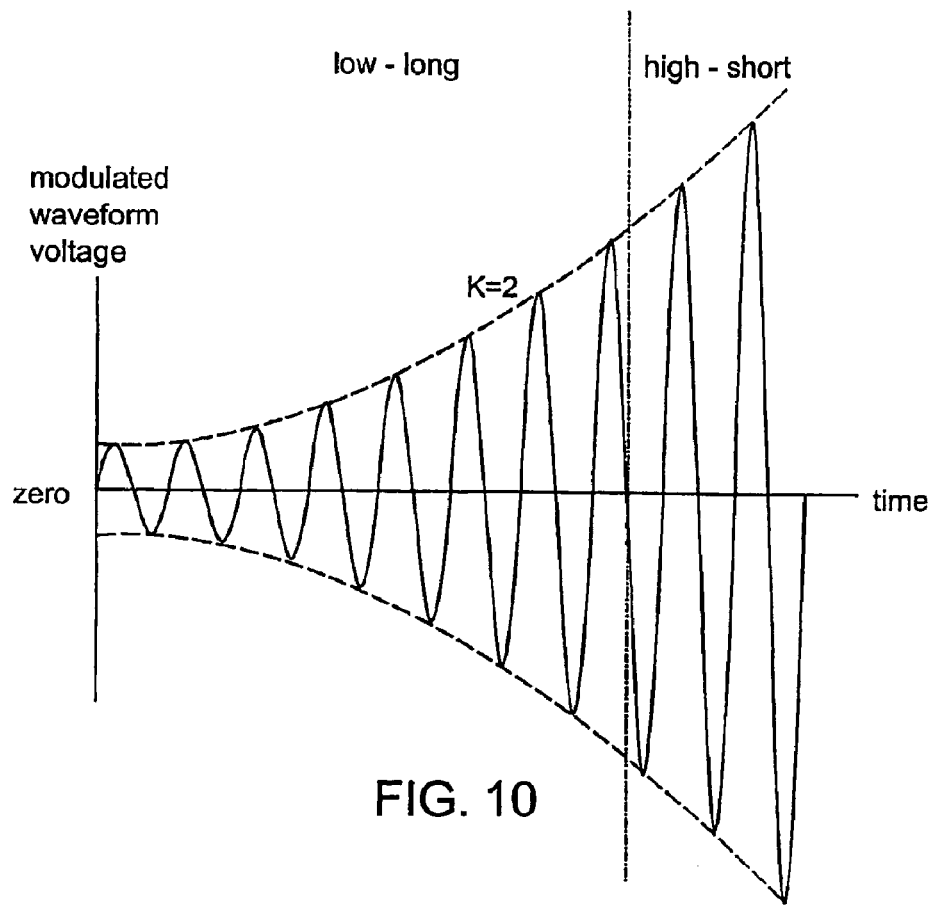
FIG. 10 shows a selected "k" modulated non-linear increasing continuous AC waveform applied as a pre-fusion electric field AC waveform as a power function with a selected power function constant "k" shown in FIG. 9, a relatively low amplitude, long duration pre-fusion electric field waveform portion is shown followed by a relatively high amplitude, short duration pre-fusion electric field waveform portion.

More specifically, with reference to FIG. 10, with a non-linear AC voltage waveform, preferably the non-linear AC voltage waveform has a relatively low AC voltage amplitude at the first portion of the waveform that brings the biological cells into close proximity and alignment. A second portion of the waveform then increases in amplitude just before the fusion pulse is to be applied. This increase in amplitude produces a short-term, intense, and non-uniform electric field, which forces the biological cells into close contact. Heating is reduced, due to the lower voltage used for alignment and the shorter duration intense AC portion.

There are a number of embodiments of this type of AC amplitude change with time, for example, exponential, logarithmic, polynomial, power function, step function, sigmoid function, and non-linear algorithm generally, etc.

One embodiment of this non-linear waveform is a power function that may be represented by the following mathematical formula or algorithm.

The amplitude of the AC waveform as a function of time=

[(Time/Total AC duration)$^k$×(Stop Amplitude—Start Amplitude)]—Start Amplitude

The total AC waveform duration, the AC starting amplitude, the AC stopping amplitude and the power exponent "k" are all optimized for the cells type being used.

Figure 9:
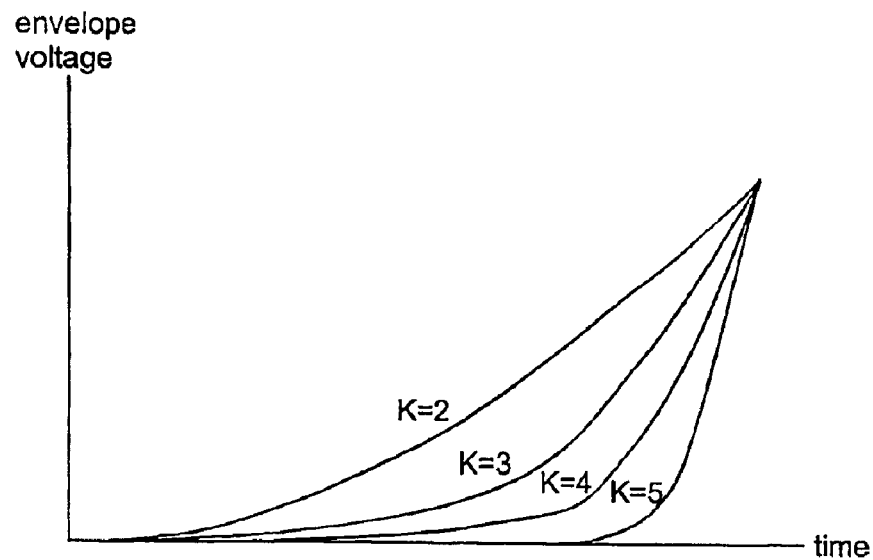
FIG. 9 shows variations in pre-fusion electric field waveforms applied to biological cells using a power function having variations in the constant "k" of the, power function. It is noted that for each selection of the constant "k", there is a relatively low amplitude, long duration pre-fusion electric field waveform portion followed by a relatively high amplitude, short duration pre-fusion electric field waveform portion.

The effect of varying the power exponent "k" is illustrated by the graphs in FIG. 9. A particular power function graph is illustrated in FIG. 10 where "k" equals 2. Thus, the invention provides a relatively low amplitude, long duration pre-fusion electric field waveform that produces a lower intensity electric field to align the biological cells and that then provides a relatively high amplitude, short duration pre-fusion electric field waveform of increased electric field intensity to force the cells into close contact, just before the AC wave ends and the cell fusion/electroporation pulses begins. This non-linear change in amplitude approach of the invention also produces less heating and less turbulence, which further provide an increase in cell hybrid production and production efficiency.

As stated above, in FIG. 10 there is a showing of non-linear, amplitude increasing continuous waveforms applied as pre-fusion electric field waveforms as a power function with a selected power function constant of "k" equals 2.

Figure 11:
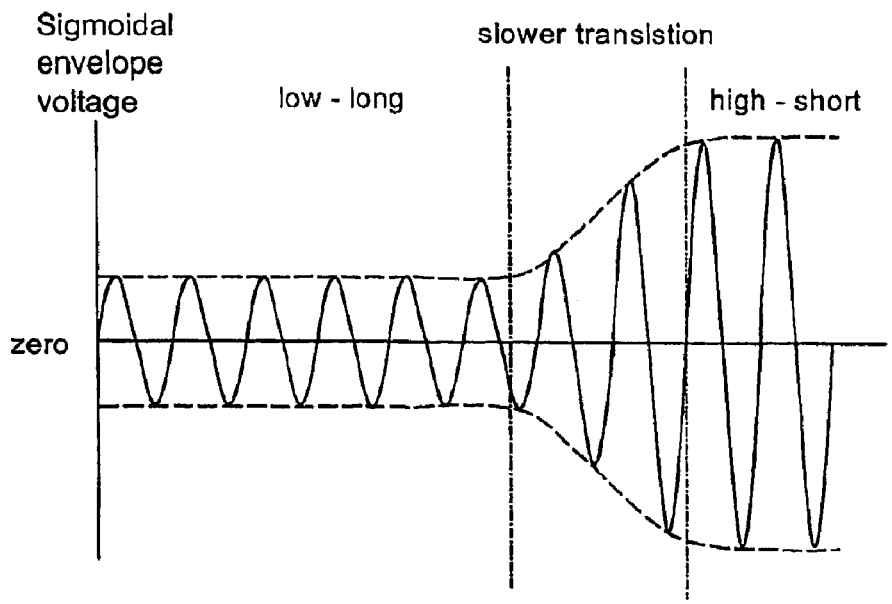
FIG. 11 shows non-linear sigmoidally shaped waveforms applied as pre-fusion electric field waveforms, wherein a transition from a relatively low amplitude, long duration pre-fusion electric field waveform to a relatively high amplitude, short duration pre-fusion electric field waveform is relatively slow.

FIG. 11 shows non-linear sigmoidally shaped waveforms, whose amplitudes change in a non-linear way, applied as pre-fusion electric field waveforms, wherein a transition from a relatively low amplitude, long duration pre-fusion electric field waveform to a relatively high amplitude, short duration pre-fusion electric field waveform is relatively slow.

Figure 12:
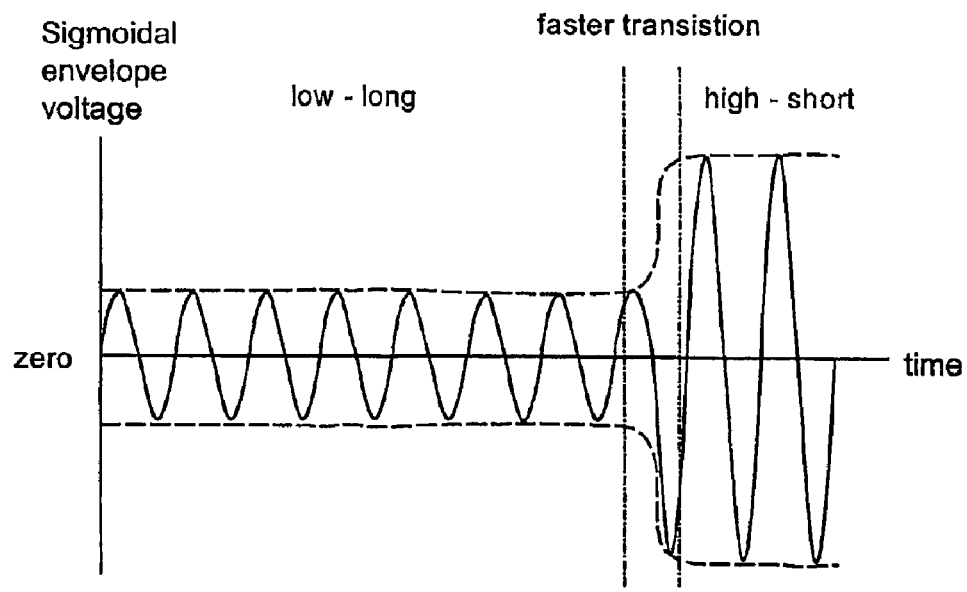
FIG. 12 shows non-linear sigmoidally shaped waveforms applied as pre-fusion electric field waveforms, wherein a transition from a relatively low amplitude, long duration pre-fusion electric field waveform to a relatively high amplitude, short duration pre-fusion electric field waveform is relatively fast.

FIG. 12 shows non-linear sigmoidally shaped waveforms, whose amplitudes change in a non-linear way, applied as pre-fusion electric field waveforms, wherein a transition from a relatively low amplitude, long duration pre-fusion electric field waveform to a relatively high amplitude, short duration pre-fusion electric field waveform is relatively fast.

Figure 13:
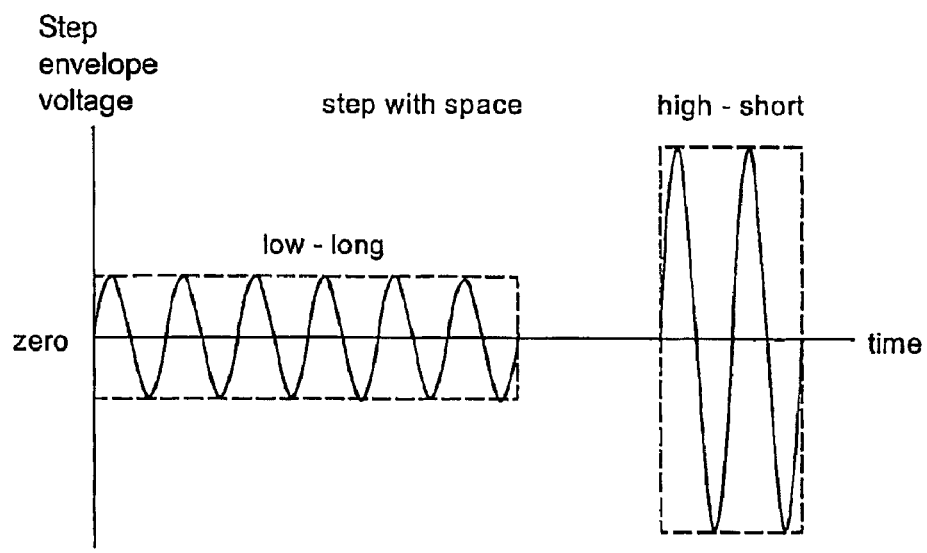
FIG. 13 shows non-linear step-wise increasing waveforms applied as pre-fusion electric field waveforms, wherein the pre-fusion electric field waveforms are provided as non-adjacent steps, wherein a first pre-fusion electric field waveform is a relatively low amplitude, long duration pre-fusion electric field waveform, wherein an off-time is provided, and wherein a second pre-fusion electric field waveform is a relatively high amplitude, short duration pre-fusion electric field-waveform.

FIG. 13 shows non-linear step-wise increasing waveforms, whose amplitudes change in a non-linear way, applied as pre-fusion electric field waveforms, wherein the pre-fusion electric field waveforms are provided as non-adjacent steps, wherein a first pre-fusion electric field waveform is a relatively low amplitude, long duration pre-fusion electric field waveform, wherein an off-time is provided, and wherein a second pre-fusion, electric field waveform is a relatively high amplitude, short duration pre-fusion electric field waveform.

Figure 14:
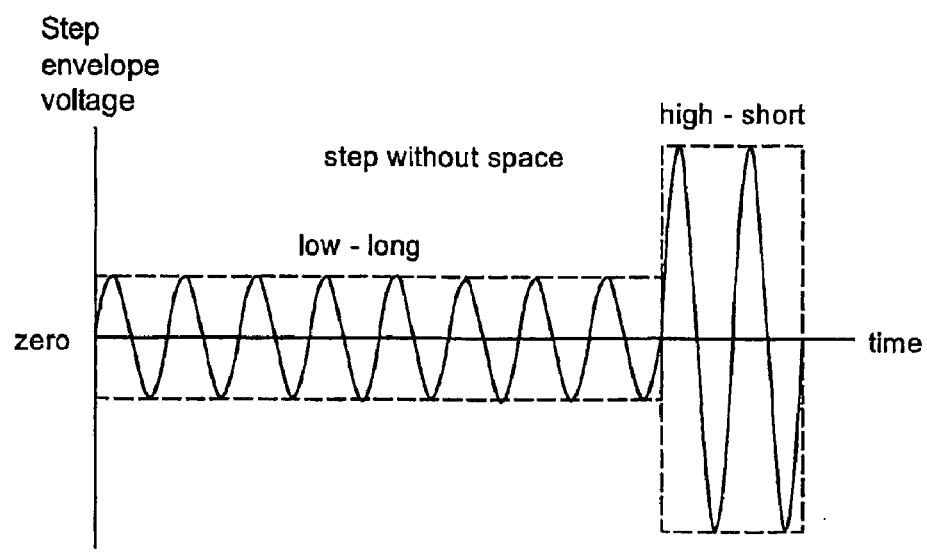
FIG. 14 shows non-linear step-wise increasing waveforms applied as pre-fusion electric field waveforms, wherein the pre-fusion electric field waveforms are provided as adjacent steps, wherein a first pre-fusion electric field waveform is a relatively low amplitude, long duration pre-fusion electric field waveform, and wherein a second pre-fusion electric field waveform is a relatively high amplitude, short duration pre-fusion electric field waveform and is applied immediately after the first pre-fusion electric field waveform.

FIG. 14 shows non-linear step-wise increasing waveforms, whose amplitudes change in a non-linear way, applied as pre-fusion electric field waveforms, wherein the pre-fusion electric field waveforms are provided as adjacent steps, wherein a first pre-fusion electric field waveform is a relatively low amplitude, long duration pre-fusion electric field waveform, and wherein a second pre-fusion electric field waveform is a relatively high amplitude, short duration pre-fusion electric field waveform and is applied immediately after the first pre-fusion electric field waveform.

The present invention can be carried out by an apparatus that delivers such pre-fusion electric field waveforms described above. In this respect, a software modification has been made to the Cyto Pulse PA-4000 system with the PA-101 AC waveform generator. This Cyto Pulse Sciences, Inc. PulseAgile (Reg. U.S. Pat. and Tm. Off.) system software now produces this waveform (see U.S. Pat. No. 6,010,613 incorporated herein by reference). The non-linear AC waveform parameters are inputted by the user, and the computer generates the AC waveforms (pre-fusion electric field waveforms) and fusion pulse waveforms (electroporation waveforms).

Experiments were carried out, and improvements of cell: fusion were recorded using stepped pre-fusion electric field waveforms whose amplitudes change in a non-linear way.

A549 cells were purchased from the ATCC. The cells were thawed and placed in tissue culture flasks with medium recommended by ATCC. Dendritic cells prepared by culture of peripheral blood mononuclear cells in a mixture of cytokines for 7 days were used as fusion partners.

8 million cells/milliliter of each cell, type were, mixed equally to yield a final concentration of 4 million cells/milliliter of each cell type in the mixture. Cell suspension volumes of 3 milliliters were used for each fusion.

The procedure consisted of the following steps. Cells were centrifuged and re-suspended in 10 milliliters of Cyto Pulse commercial Cytofusion medium (formula C) The cells were washed twice in the same medium and re-suspended in Cytofusion medium after the washes. Cells were counted and the cell concentration was adjusted to 8 million cells/milliliter. Equal volumes of A549 cells and dendritic cells were mixed. Three milliliters of cell suspension was placed into a 6 milliliter capacity coaxial cell fusion electrode, having an internal cylindrical anode of 3.9 cm diameter with a gap of 4 mm from the cathode. The following cell fusion protocols were applied.

The parameters for the two experimental and one control groups are as follows:
Group A: (Invention)
First pre-fusion electric field waveform: 45 V to 45 V, 20 Seconds, 0.8 MHz
Second pre-fusion electric field waveform: 75 V to 75 V. 10 seconds, 0.8 MHz
Fusion/electroporation pulse 1×800 V, 40 microseconds
Post fusion/electroporation pulse 45 V to 45 V, 50 seconds, 0.8 MHz
Group B: (Prior Art)
First pre-fusion electric field waveform: 75 V to 75 V. 10 seconds, 0.8 MHz
Fusion/electroporation pulse 1×800 V, 40 microseconds
Post fusion/electroporation pulse 45 V to 45 V, 50 seconds, 0.8 MHz
Group C: (Control—No Electricity)
After fusion, cells were left undisturbed for 30 minutes to allow fusion maturation. Three milliliters of tissue culture medium with 10% fetal bovine serum were added to the cell suspension in the cell fusion electrode. Fifteen minutes later the cells were harvested for analysis.

An aliquot of cells was placed onto a silinized microscope slide using a commercial Cytospin (Shandon) centrifuge. The cells were identified using immunohistochemistry. A549 cells were identified using anti-keratin monoclonal antibodies and the dendritic cells were identified by using anti human HLA-DR monoclonal antibodies. Meyers hematoxylain was used for a nuclear counterstain. The cells with either brown keratin staining or red HLA-DR staining or both were manually counted.

Results are shown in the TABLE below in which percentages of fused cells are presented for mixed A549 and dendritic cells in Group A (which were treated with a pre-fusion electric field waveform of the invention prior to cell fusion), for mixed A549 and dendritic cells in Group B (which were treated by a prior art pre-fusion electric field waveform prior to cell fusion), and for mixed A549 and dendritic cells in Group C (which were pot treated by any pre-fusion electric field waveform at all prior to cell fusion).

TABLE

| Group | Fused A549/A549 | Fused den./den. | Fused den./A549 |
|---|---|---|---|
| A (Invention) | 7.2% | 5.4% | 22.7% |
| B (Pr.Art) | 6.8% | 4.0% | 18.1% |
| C (Control) | 2.2% | 2.2% | 10.8% |

By way of explanation of the TABLE, the first column lists the respective groups of A549 and dendritic cells (den.) that were subjected to fusion treatment. The second column lists the percentages of fused cells formed by the fusion of an A549 cell with another A549 cell. The third column lists percentages of fused cells formed by the fusion of a dendritic cell with another dendritic cell. The fourth column lists percentages of fused cells formed by the fusion of a dendritic cell with an A549 cell.

It is noted that for each type of cell fusion (A549/A549, den./den., and den./A549), the percentages of fused cells are greater with Group A (employing a pre-fusion electric field waveform of the invention) than with either Group B (employing a pre-fusion electric field waveform of the prior art) or Group C (employing no pre-fusion electric field waveform at all). More specifically, 7.2% is greater than 6.8%, which is greater than 2.2%. Also, 5.4% is greater than 4.0%, which is greater than 2.2%. Also, 22.7% is greater than 18.1%, which is greater than 10.8%. In summary, employing a pre-fusion electric field waveform of the invention provides higher fusion efficiency than employing either a prior art pre-fusion electric field waveform or no pre-fusion electric field waveform at all.

As to the manner of usage and operation of the present invention, the same is apparent from the above disclosure, and accordingly, no further discussion relative to the manner of usage and operation need be provided.

It is apparent from the above that the present invention accomplishes all of the objects set forth by providing new and improved non-linear dielectrophoresis waveforms for cell fusion which may advantageously be used to provide pre-fusion electric field waveforms for biological cells which increase cell fusion efficiency over biological cells treated with a constant amplitude or a linearly increasing amplitude pre-fusion electric field waveform. With the invention, non-linear dielectrophoresis waveforms avoid the mechanical forces, turbulence, and heating which result from immediately applying a high amplitude alignment waveform to biological cells that are to undergo cell fusion. With the invention, non-linear dielectrophoresis waveforms reduce heating of biological cells being treated with pre-fusion electric field waveforms for increasing cell alignment and cell membrane contact prior to being subjected to cell fusion. With the invention, non-linear dielectrophoresis waveforms increase cell membrane contact between biological cells treated with pre-fusion electric field waveforms prior to undergoing cell fusion.

Thus, while the present invention has been shown in the drawings and fully described above with particularity and detail in connection with what is presently deemed to be the most practical and preferred embodiment(s) of the invention, it will be apparent to those of ordinary skill in the art that many modifications thereof may be made without departing from the principles and concepts set forth herein, including, but not limited to, variations in size, materials, shape, form, function and manner of operation, assembly and use.

What is claimed is:

1. A method of fusing or electroporating biological cells comprising the steps of:

treating the biological cells with a pre-fusion electric field waveform which changes amplitude in a non-linear way with respect to time, and followed by subjecting the biological cells to a fusion or electroporation pulse.

2. The method of claim 1 wherein the biological cells are first aligned and then compressed resulting in increased cell membrane contact prior to being subjected to cell fusion.

3. The method of claim 1 wherein the pre-fusion electric field waveform amplitude includes a relatively low amplitude, long duration electric field waveform followed by a relatively high amplitude, short duration electric field waveform.

4. The method of claim 1 wherein the pre-fusion electric field waveform amplitude changes in a stepped non-linear way with respect to time.

5. The method of claim 1 wherein the pre-fusion electric field waveform amplitude changes in a continuous non-linear way with respect to time.

6. The method of claim 1 wherein the pre-fusion electric field waveform includes an AC electric field waveform which changes amplitude in a non-linear way with respect to time.

7. The method at claim 6 wherein the amplitude of said AC electric field waveform changes in a non-linear way with respect to time in accordance with a non-linear algorithm.

8. The method of claim 6 wherein said AC electric field waveform has an AC-waveform electric field intensity between 10 volts/cm and 1,000 volts/cm.

9. The method of claim 1 wherein the pre-fusion electric field waveform amplitude includes non-linear step-wise increasing waveforms applied as pre-fusion electric field waveforms, and wherein the waveforms are provided as either adjacent steps or non-adjacent steps.

10. The method of claim 1, further including the steps of:

treating the biological cells with an AC electric field waveform following the cell fusion or electroporation pulse.

11. A method of treating biological cells prior to subjecting the biological cells to cell fusion, comprising the step of:

treating the biological cells with an electric field amplitude which changes in a non-linear way with respect to time, such that the biological cells are aligned and have increased cell membrane contact, and such that the biological cells are compressed against one another prior to being subjected to cell fusion.

12. The method of claim 1, further comprising the step of subjecting the biological cells to a post-fusion or post-electroporation electric field waveform.

* * * * *